United States Patent
Lorenz, deceased et al.

[11] 4,054,650
[45] Oct. 18, 1977

[54] O,O-DIETHYL-O-[N-METHOXY-2-NITROBENZIMIDOYL]-THIONO-PHOSPHORIC ACID ESTERS

[75] Inventors: Walter Lorenz, deceased, late of Wuppertal, Germany, by Erika Lorenz, heiress; Ingeborg Hammann, Cologne, Germany; Wolfgang Behrenz, Overath, Germany; Bernhard Homeyer, Leverkusen, Germany

[73] Assignee: Bayer Aktiengesellschaft, Leverkusen, Germany

[21] Appl. No.: 726,362

[22] Filed: Sept. 24, 1976

[30] Foreign Application Priority Data
Oct. 7, 1975 Germany .................. 2544776

[51] Int. Cl.² .................. A01N 9/36; C07F 9/165
[52] U.S. Cl. .................. 424/211; 260/944
[58] Field of Search .................. 260/944; 424/211

[56] References Cited
U.S. PATENT DOCUMENTS
3,760,041  9/1973  Lorenz et al. .................. 260/944

Primary Examiner—Richard L. Raymond
Attorney, Agent, or Firm—Burgess, Dinklage & Sprung

[57] ABSTRACT

O,O-Diethyl-O-[N-methoxy-2-nitrobenzimidoyl]-thiono-phosphoric acid ester of the formula (I)

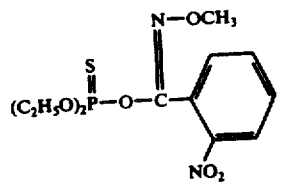

which possesses insecticidal and acaricidal properties.

3 Claims, No Drawings

O,O-DIETHYL-O-[N-METHOXY-2-NITROBEN-ZIMIDOYL]-THIONO-PHOSPHORIC ACID ESTERS

The present invention relates to and has for its objects the provision of the particular new compound O,O,-diethyl-O-[N-methoxy-2-nitrobenzimidoyl]-thionophosphoric acid ester which possesses insecticidal and acaricidal properties, active compositions in the form of mixtures of such compound with solid and liquid dispersible carrier vehicles, and methods for producing such compound and for using such compound in a new way especially for combating pests, e.g. insects and acarids, with other and further objects becoming apparent from a study of the within specification and accompanying examples.

It is known from U.S. Pat. No. 3,760,041 that some O-(N-alkoxy-benzimidoyl)-thionophosphoric acid esters, for example, O,O-diethyl-O-(N-methoxy-benzimidoyl- (Compound A) and N-ethoxy-4-nitrobenzimidoyl)-thionophosphoric acid ester (Compound B), are distinguished by an insecticidal and acaricidal activity.

The present invention provides O,O-diethyl-O-(N-methoxy-2-nitrobenzimidoyl)-thionophosphoric acid ester of the formula

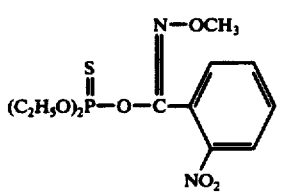

(I)

Surprisingly, the O,O-diethyl-O-(N-methoxy-2-nitrobenzimidoyl)-thionophosphoric acid ester according to the invention exhibits a substantially better insecticidal and acaricidal action than the known O-(N-alkoxybenzimidoyl)-thionophosphoric acid esters of analogous structure and of the same type of action. The product according to the present invention thus represents a genuine enrichment of the art.

The invention also provides a process for the production of O,O-diethyl-O-(N-methoxy-2-nitrobenzimidoyl)-thionophosphoric acid ester of the formula (I) in which an O,O-diethylthionophosphoric acid diester halide of the formula

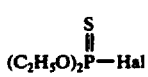

(II)

in which

Hal represents halogen, preferably chlorine, is reacted with N-methoxy-2-nitrobenzyhydroxamic acid of the formula

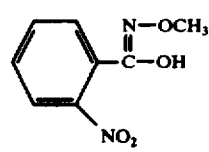

(III)

in the form of an alkali metal salt, alkaline earth metal salt or ammonium salt, or in the presence of an acid acceptor, and optionally in the presence of a solvent or diluent.

If O,O-diethyl-thionophosphoric acid ester chloride and N-methoxy-2-nitrobenzyhydroxamic acid are used as starting materials, the course of the reaction can be represented by the following formula scheme:

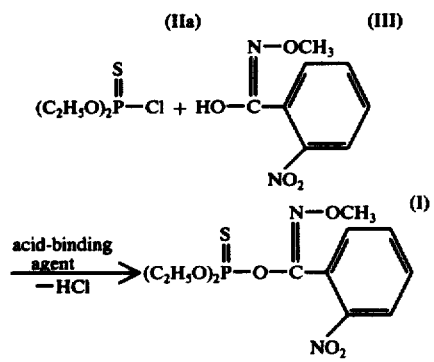

The O,O-diethylthionophosphoric acid diester halide (II) required as a starting material is known from the literature and can be prepared, as can the N-methoxy-benzyhydroxamic acid derivative (III), in accordance with generally known processes; the latter compound can be prepared, for example, from the corresponding benzyhydroxamic acid by reaction with alcoholic potassium hydroxide solution and alkyl iodide according to Waldstein: Ann. 181, 385, or, for example, from benzoyl chloride and the alkoxylamine per Gierke, Ann. 205, 278.

The reaction according to the present invention is preferably carried out in the presence of a solvent or diluent. Practically all inert organic solvents can be used for this purpose. These include, in particular, aliphatic and aromatic (optionally chlorinated) hydrocarbons, for example benzene, toluene, xylene, benzine, methylene chloride, chloroform, carbon tetrachloride and chlorobenzene; ethers, for example diethyl ether, dibutyl ether and dioxane; ketones, for example acetone, methyl ethyl ketone, methyl isopropyl ketone and methyl isobutyl ketone; and nitriles, for example acetonitrile and propionitrile.

All customary acid-binding agents can be used as the acid acceptors. Alkali metal carbonates and alkali metal alcoholates, such as sodium carbonate and potassium carbonate, sodium methylate and ethylate and potassium methylate and ethylate have proved particularly suitable, as have potassium chloride, and also aliphatic, aromatic or heterocyclic amines, for example triethylamine, trimethylamine, dimethylaniline, dimethylbenzylamine and pyridine.

The reaction temperature can be varied within a substantial range. In general, a temperature of 0° to 100° C, preferably 40° to 70° C, is used. The reaction is in general carried out under normal pressure.

In carrying out the process, the benzhydroxamic acid component (III) is preferably employed in 10–20% excess. In most cases, the benzyhydroxamic acid component and the acid acceptor are first introduced into a solvent and the phosphoric acid ester component is added dropwise at the stated temperatures. After several hours' reaction at elevated temperature, the mixture may be worked up in the usual manner, either by introducing the cooled batch into water, whereupon a crystalline precipitate forms rapidly, which precipitate is filtered off, or by extracting the aqueous phase by shaking with an organic solvent. The organic layer may be separated off and then worked up in the generally customary manner by washing, drying and distilling off the solvent.

The new compound is obtained in a crystalline form and can be characterized by its melting point.

As already mentioned, the new O,O-diethyl-O-(N-methoxy-2-nitrobenzimidoyl)-thionophosphoric acid ester is distinguished by an excellent insecticidal and acaricidal activity against plant pests, hygiene pests and pests of stored products. The compound possesses a good action against both sucking and biting insects and mites (Acarina).

For this reason, the compound according to the invention can be employed successfully as a pesticide in plant protection as well as in the hygiene field and the field of protection of stored products.

The active compound according to the invention may be used in the form of the usual types of commercially available formulations and/or in the other application forms prepared from these formulations.

The active compound is well tolerated by plants, has a favorable level of toxicity to warm-blooded animals, and can be used for combating animal pests, especially insects and arachnida which are encountered in agriculture, in forestry, in the protection of stored products and of materials, and in the hygiene field. It is active against normally sensitive and resistant species and against all or some stages of development. The above-mentioned pests include:

From the order of Isopoda, for example, *Oniscus asellus, Armadillidium vulgare* and *Porcellio scaber*. From the order of the Diplopoda, for example, *Blaniulus guttulatus*. From the order of the Chilopoda, for example, *Geophilus carpophagus* and *Scutigera spec*. From the order of the Symphyla, for example, *Scutigerella immaculata*. From the order of the Thysanura, for example, *Lepisma saccharina*. From the order of the Collembola, for example, *Onychiurus armatus*. From the order of the Orthoptera, for example, *Blatta orientalis, Periplanetaamericana, Leucophaea maderae, Blattella germanica, Acheta domesticus, Grylloptalpa* spp., *Locusta migratoria migratorioides, Melanoplus differentialis* and *Schistocerca gregaria*. From the order of the Dermaptera, for example, *Forficula auricularia*. From the order of the Isoptera, for example, *Reticulitermes* spp. From the order of the Anoplura, for example, *Phylloxera vastatrix, Pemphigus* spp., *Pediculus humanus corporis, Haematopinus* spp. and *Linognathus* spp. From the order of the Mallophaga, for example, *Trichodectes* spp. and *Damalinea* spp. From the order of the Thysanoptera, for example, *Hercinothrips femoralis* and *Thrips tabaci*. From the order of the Heteroptera, for example, *Eurygaster* spp., *Dysdercus intermedius, Piesma quadrata, Cimex lectularius. Rhodnius prolixus* and *Triatoma* spp. From the order of the Homoptera, for example, *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, Macrosiphum avenae, Myzus* spp., *Phorodon humuli, Rhopalosiphum padi, Empoasca* spp., *Euscelis bilobatus, Nephotettix cincticeps, Lecanium corni, Saissetia oleae, Laodelphax striatellus, Nilaparvata lugens, Aonidiella aurantii, Aspidiotus hederae, Pseudococcus* spp. and *Psylla* spp.. From the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea, Lymantria* spp., *Bucculatrix thruberiella, Phyllocnistis citrella, Agrotis* spp., *Euxoa* spp., *Feltia* spp., *Earias insulana, Heliothis* spp., *Laphygma exigua, Mamestra brassicae, Panolis flammea, Prodenia litura, Spodoptera* spp., *Trichoplusia ni, Carpocapsa pomonella, Pieris* spp., *Chilo* spp, *Pyrausta nubilalis, Ephestia kuhniella, Galleria mellonella, Cacaecia podana, Capua reticulana, Choristoneura fumiferana, Clysia ambiguella, Homona magnanima* and *Tortrix viridana*. From the order of the Coleoptera, for example, *Anobium punctatum, Rhizopertha dominica, Bruchidius obtectus, Acanthoscelides obtectus, Hylotrupes bajulus, Agelastica alni, Leptinotarsa decemlineata, Phaedon cochleariae, Diabrotica* spp., *Psylliodes chrysocephala, Epilachna varivestis, Atomaria* spp., *Oryzaephilus surinamensis, Anthonomus* spp., *Sitophilus* spp., *Otiorrhynchus sulcatus, Cosmopolites sordidus, Ceuthorrhynchus assimilis, Hypera postica, Dermestes* spp., *Trogoderma* spp., *Anthrenus* spp., *Attagenus* spp., *Lyctus* spp., *Meligethes aeneus, Ptinus* spp., *Niptus hololeucus, Gibbium psylloides, Tribolium* spp., *Tenebrio molitor, Agriotes* spp., *conoderus* spp., *Melolontha melolontha, Amphimallon solstitialis* and *Costelytra zealandica*. From the order of the Hymenoptera, for example, *Diprion* spp., *Hoplocampa* spp., *Lasius* spp., *Monomorium pharaonis* and *Vespa* spp. From the order of the Diptera, for example, *Aedes* spp., *Anopheles* spp., *Culex* spp., *Drosophila melanogaster, Musca* spp., *Fannia* spp., *Calliphora erythrocephala, Lucilia* spp., *Chrysomyia* spp., *Cuterebra* spp., *Gastrophilus* spp., *Hyppobosca* spp., *Stomoxys* spp., *Oestrus* spp., *Hypoderma* spp., *Tabanus* spp., *Tannia* spp., *Bibio hortulanus, Oscinella frit, Phorbia* spp., *Pegomyia hyoscyami. Ceratitis capitata, Dacus oleae* and *Tipula paludosa*. From the order of the Siphonaptera, for example, *Xenopsylla cheopis* and *Ceratophyllus* spp.. From the order of the Arachnida, for example, *Scorpio maurus* and *Latrodectus mactans*. From the order of the Acarina, for example, *Acarus siro, Argas* spp., *Ornithodoros* spp., *Dermanyssus gallinae, Eriophyes ribis, Phyllocoptruta oleivora, Boophilus* spp., *Rhipicephalus* spp., *Ambluomma* spp., *Hyaloma* spp., *Ixodes* spp., *Psoroptes* spp., *Chorioptes* spp., *Sarcoptes* spp., *Tarsoneums* spp., *Bryobia praetiosa, Panonychus* spp. and *Tetranychus* spp., When used against hygiene pests and pests of stored products, the active compounds are distinguished by an excellent residual activity on wood and clay as well as a good stability to alkali on limed substrates.

The active compounds according to the instant invention can be utilized, if desired, in the form of the usual formulations or compositions with conventional inert (i.e., plant compatible or herbicidally inert) pesticide diluents or extenders, i.e., diluents, carriers or extenders of the type usuable in conventional pesticide formulations or compositions, e.g., conventional pesticide dispersible carrier vehicles such as gases, solutions, emulsions, wettable powders, suspensions, powders, dusting agents, foams, pastes, soluble powders, granules, aerosols, suspension-emulsion concentrates, seed-treatment powders, natural and synthetic materials impregnated with active compound, very fine capsules in polymeric substances and in coating compositions, for use on seed, and formulations used with burning equipment, such as fumigating cartridges, fumigating cans, fumigating coils and the like, as well as ULV cold mist and warm mist formulations.

These are prepared in known manner, for instance by extending the active compounds with conventional pesticide dispersible liquid diluent carriers and/or dispersible solid carriers optionally with the use of carrier vehicle assistants, e.g., conventional pesticide surface-active agents, including emulsifying agents and/or dispersing agents, whereby, for example, in the case where water is used as diluent, organic solvents may be added as auxiliary solvents. The following may be chiefly considered for use as conventional carrier vehicles for this purpose: aerosol propellants which are gaseous at normal temperatures and pressures, such as halogenated hydrocarbons as well as butane, propane, nitrogen and carbon dioxide; inert dispersible liquid diluent carriers, including inert organic solvents, such as aromatic hydrocarbons (e.g., benzene, toluene, xylene, alkyl naphthalenes, etc.), halogenated, especially chlorinated, aromatic hydrocarbons (e.g., chlorobenzenes, etc.), cycloalkanes, (e.g., cyclohexane, etc.), paraffins (e.g., petroleum or mineral oil fractions), chlorinated aliphatic hydrocarbons (e.g., methylene chloride, chloroethylenes, etc.), alcohols (e.g., methanol, ethanol, propanol, butanol, glycol, etc.) as well as ethers and esters thereof (e.g., glycol monomethyl ether, etc.), amines (e.g., ethanolamine, etc.), amides (e.g., dimethyl formamide, etc.), sulfoxides (e.g., dimethyl sulfoxide, etc.), acetonitrile ketones (e.g., acetone, methyl ethyl ketone, methyl isobutyl ketone, cyclohexanone, etc.), and/or water; as solid carriers, ground natural minerals, such as kaolins, clays, talc, chalk, quartz, attapulgite, montmorillonite or diatomaceous earth, and ground synthetic minerals, such as highly dispersed silicic acid, alumina and silicates; as solid carriers for granules; crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; whereas the following may be chiefly considered for use as conventional carrier vehicle assistants, e.g., surface-active agents, for this purpose: emulsifying agents, such as non-ionic and/or anionic emulsifying agents (e.g., polyethylene oxide esters of fatty acids, polyethylene oxide ethers of fatty alcohols, alkyl sulfates, alkyl sulfonates, aryl sulfonates, albumin hydrolyzates, etc., and especially alkyl arylpolyglycol ethers, magnesium stearate, sodium oleate, etc.); and/or dispersing agents, such as lignin, sulfite waste liquors, methyl cellulose, etc.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts or iron, manganese, boron, copper, cobalt, molybdenum and zinc.

Such active compound may be employed alone or in the form of mixtures with one another and/or with such solid and/or liquid dispersible carrier vehicles and/or with other known compatible active agents, especially plant protection agents, such as other insecticides and acaricides, or nematicides, fungicides, bactericides, rodenticides, herbicides, fertilizers, growth-regulating agents, etc., if desired, or in the form of particular dosage preparations for specific application made therefrom, such as solutions, emulsions, suspensions, powders, pastes, and granules which are thus ready for use.

As concerns commercially marketed preparations, these generally contemplate carrier composition mixtures in which the active compound is present in an amount substantially between about 0.1–95% by weight, and preferably 0.5–90% by weight, of the mixture, whereas carrier composition mixtures suitable for direct application or field application generally contemplate those in which the active compound is present in an amount substantially between about 0.0000001–100, preferably 0.01–10%, by weight of the mixture. Thus, the present invention contemplates overall compositions which comprise mixtures of a conventional dispersible carrier such as (1) a dispersible inert finely divided carrier solid, and/or (2) a dispersible carrier liquid such as an inert organic solvent and/or water, preferably including a surface-active effective amount of the carrier vehicle assistant, e.g. a surface-active agent, such as an emulsifying agent and/or a dispersing agent, and an amount of the active compound which is effective for the purpose in question and which is generally between about 0.0001–95%, and preferably 0.01–95%, by weight of the mixture.

The active compounds can also be used in accordance with the well known ultra-low-volume process with good success, i.e., by applying such compound if normally a liquid, or by applying a liquid composition containing the same, via very effective atomizing equipment, in finely divided form, e.g., average particle diameter of from 50–100 microns, or even less, i.e., mist form, for example by airplane crop spraying techniques. Only up to at most about a few liters/hectare are needed, and often amounts only up to about 15 to 1000 g/hectare, preferably 40 to 600 g/hectare, are sufficient. In this process it is possible to use highly concentrated liquid compositions with said liquid carrier vehicles containing from about 20 to about 95% by weight of the active compound or even the 100% active substance alone, e.g., about 20–100% by weight of the active compound.

Furthermore, the present invention contemplates methods of selectively killing, combating or controlling pests, e.g., insects and acarids, which comprises applying to at least one of correspondingly (a) such insects, (b) such acarids, and (c) the corresponding habitat thereof, i.e., the locus to be protected, e.g., to a growing crop, to an area where a crop is to be grown or to a domestic animal, a correspondingly combative or toxic amount, i.e. an insecticidally or acaricidally effective amount, of the particular active compound of the invention alone or together with a carrier vehicle as noted above. The instant formulations or compositions are applied in the usual manner, for instance by spraying, atomizing, vaporizing, scattering, dusting, watering, squirting, sprinkling, pouring, fumigating, and the like.

It will be realized, of course, that the concentration of the particular active compound utilized in admixture with the carrier vehicle will depend upon the intended application. Therefore, in special cases it is possible to go above or below the aforementioned concentration ranges.

The unexpected superiority and outstanding activity of the particular new compounds of the present invention are illustrated, without limitation, by the following examples:

EXAMPLE 1

Tetranychus test (resistant)

Solvent: 3 parts by weight of acetone

Emulsifier: 1 part by weight of alkylaryl polyglycol ether.

To produce a suitable preparation of active compound, 1 part by weight of the active compound was mixed with the stated amount of solvent and the stated amount of emulsifier and the concentrate was diluted with water to the desired concentration.

Bean plants (*Phaseolus vulgaris*) which were heavily infested with the common or two-spotted spider mite (*Tetranychus urticae*) in all stages of development were sprayed with the preparation of the active compound until dripping wet.

After the specified periods of time, the degree of destruction was determined as a percentage: 100% means that all the spider mites were killed whereas 0% means that none of the spider mites were killed.

The active compounds, the concentrations of the active compounds, the evaluation times and the results can be seen from the following Table 1:

Table 1

(*Tetranychus* test)

| Active compound | Active compound concentration in % | Degree of destruction in % after 2 days |
|---|---|---|
| 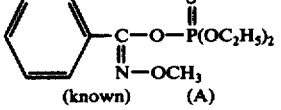 (known) (A) | 0.1 | 0 |
| 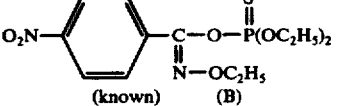 (known) (B) | 0.1 | 0 |
| 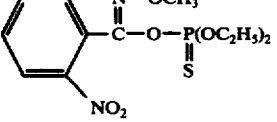 (I) | 0.1 | 100 |

EXAMPLE 2

Phaedon larvae test

Solvent: 3 parts by weight of acetone

Emulsifier: 1 part by weight of alkylaryl polyglycol ether

To produce a suitable preparation of active compound, 1 part by weight of the active compound was mixed with the stated amount of solvent containing the stated amount of emulsifier and the concentrate was diluted with water to the desired concentration.

Cabbage leaves (*Brassica oleracea*) were sprayed with the preparation of the active compound until dripping wet and were then infested with mustard beetle larvae (*Phaedon cochleariae*).

After the specified periods of time, the degree of destruction was determined in %. 100% means that all beetle larvae had been killed whereas 0% means that none of the beetle larvae had been killed.

The active compounds, the concentrations of the active compounds, the evaluation times and the results can be seen from the following Table 2:

Table 2

(*Phaedon* larvae test)

| Active compound | Active compound concentration in % | Degree of destruction in % after 3 days |
|---|---|---|
| 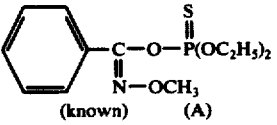 (known) (A) | 0.02<br>0.004<br>0.0008 | 100<br>35<br>0 |
| 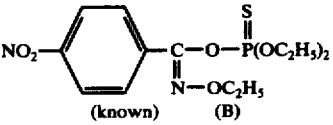 (known) (B) | 0.02<br>0.004<br>0.0008 | 100<br>100<br>0 |
| 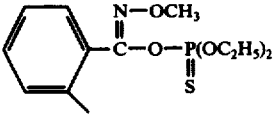 (I) | 0.02<br>0.004<br>0.0008 | 100<br>100<br>100 |

EXAMPLE 3

Laphygma test

Solvent: 3 parts by weight of acetone

Emulsifier: 1 part by weight of alkylaryl polyglycol ether

To produce a suitable preparation of active compound, 1 part by weight of the active compound was mixed with the stated amount of solvent and the stated amount of emulsifier and the concentrate was diluted with water to the desired concentration.

Cotton leaves (*Gossypium hirsutum*) were sprayed with the preparation of the active compound until dew-moist and were then infested with caterpillars of the owlet moth (*Laphygma exigua*).

After the specified periods of time, the destruction in % was determined. 100% means that all caterpillars had been killed whilst 0% indicates that no caterpillars had been killed.

The active compounds, the concentrations of the active compounds, the evaluation times and the results can be seen from the following Table 3:

Table 3

(*Laphygma* test)

| Active Compound | Active compound concentration in % | Degree of destruction in % after 3 days |
|---|---|---|
| 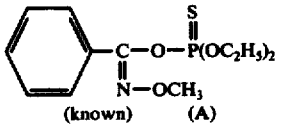 (known) (A) | 0.02<br>0.004 | 100<br>0 |
| 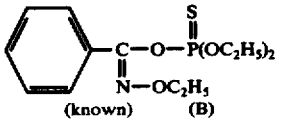 (known) (B) | 0.02<br>0.004<br>0.0008 | 100<br>30<br>0 |

Table 3-continued (*Laphygma* test)

| Active Compound | Active compound concentration in % | Degree of destruction in % after 3 days |
|---|---|---|
| ![structure: benzene ring with N—OCH₃, C—O—P(OC₂H₅)₂ with =S, and NO₂ substituent] (I) | 0.02<br>0.004<br>0.0008 | 100<br>100<br>60 |

EXAMPLE 4

Test insect: *Tenebrio molitor* larvae in the soil
Solvent: 3 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

The preparation of active compound was intimately mixed with the soil. The concentration of the active compound in the preparation was practically immaterial, the only decisive factor being the amount by weight of active compound per unit volume of soil, which is quoted in ppm (= mg/l). The soil was filled into pots and the pots were left to stand at room temperature.

After 24 hours the test insects were introduced into the treated soil and after a further 2 to 7 days the degree of effectiveness of the active compound was determined in % by counting the dead and live test insects. The degree of effectiveness was 100% if all test insects had been killed and was 0% if exactly as many test insects were still alive as in the case of the untreated control.

The active compounds, amounts used and results can be seen from the Table 4 which follows:

Table 4

(*Tenebrio molitor* larvae in the soil)

| Active compound | Degree of destruction in % at an active compound concentration of 2.5 ppm |
|---|---|
| (C₂H₅O)₂P(=S)—O—C(=NOC₂H₅)—C₆H₄—NO₂ (known) (B) | 0 |
| (C₂H₅O)₂P(=S)—O—C(=NOCH₃)—C₆H₄—NO₂ (I) | 100 |

EXAMPLE 5

Test insect: *Phorbia antiqua* grubs in the soil
Solvent: 3 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

The preparation of active compound was intimately mixed with the soil. The concentration of the active compound in the preparation was practically immaterial, the only decisive factor being the amount by weight of active compound per unit volume of soil, which is quoted in ppm (= mg/l). The soil was filled into pots and the pots were left to stand at room temperature.

After 24 hours the test insects were introduced into the treated soil and after a further 2 to 7 days the degree of effectiveness of the active compound was determined in % by counting the dead and live test insects. The degree of effectiveness was 100% if all test insects had been killed and was 0% if exactly as many test insects were still alive as in the case of the untreated control.

The active compounds, amounts used and results can be seen from the Table 5 which follows:

Table 5

(*Phorbia antiqua* grubs in the soil)

| Active compound | Degree of destruction in % at an active compound concentration of 2.5 ppm |
|---|---|
| (C₂H₅O)₂P(=S)—O—C(=NOC₂H₅)—C₆H₄—NO₂ (known) (B) | 0 |
| (C₂H₅O)₂P(=S)—O—C(=NOCH₃)—C₆H₄—NO₂ (I) | 100 |

EXAMPLE 6

Test insects: *Sitophilus granarius*
Solvent: Acetone 2 parts by weight of the active compound were taken up in 1,000 parts by volume of the solvent. The solution so obtained was diluted with further solvent to the desired concentrations.

2.5 ml of the solution of the active compound were pipetted into a Petri dish. On the bottom of the Petri dish there was a filter paper with a diameter of about 9.5 cm. The Petri dish remained uncovered until the solvent had completely evaporated. The amount of active compound per m² of filter paper varied with the concentration of the solution of active compound. About 25 test insects were then placed in the Petri dish and it was covered with a glass lid.

The condition of the test insects was observed 3 days after the commencement of the experiment. The destruction, in %, was determined. 100% denotes that all test insects had been killed; 0% denotes that no test insects had been killed.

The active compounds, the concentrations of the active compounds, the test insects and the results can be seen from the following Table 6:

Table 6

| (Sitophilus granarius) | | |
|---|---|---|
| Active compound | Active Compound concentration in % | Degree of destruction in % |
| (A) (known) C₆H₅–C(=N-OCH₃)–O–P(S)(OC₂H₅)₂ | 0.2<br>0.02 | 100<br>0 |
| (B) (known) O₂N–C₆H₄–C(=N-OC₂H₅)–O–P(S)(OC₂H₅)₂ | 0.02<br>0.002 | 100<br>0 |
| (I) 2-NO₂-C₆H₄–C(=N-OCH₃)–O–P(S)(OC₂H₅)₂ | 0.002 | 100 |

EXAMPLE 7

LT₁₀₀ test for Diptera
Test insects: *Aedes aegypti*
Solvent: Acetone 2 parts by weight of active compound were dissolved in 1,000 parts by volume of solvent. The solution so obtained was diluted with further solvent to the desired lower concentrations.

2.5 ml of the solution of active compound were pipetted into a Petri dish. On the bottom of the Petri dish there was a filter paper with a diameter of about 9.5 cm. The Petri dish remained uncovered until the solvent had completely evaporated. The amount of active compound per m² of filter paper varied with the concentration of the solution of active compound. About 25 test insects were then placed in the Petri dish and it was covered with a glass lid.

The condition of the test insects was continuously observed. The time which was necessary for 100% destruction was determined.

The test insects, the active compounds, the concentrations of the active compounds and the times at which there was a 100% destruction can be seen from the following Table 7:

Table 7

| (LT₁₀₀ test for Diptera/*Aedes aegypti*) | | |
|---|---|---|
| Active compound | Active compound concentration of the solution in % | LT₁₀₀ in minutes (') |
| (A) (known) C₆H₅–C(=N-OCH₃)–O–P(S)(OC₂H₅)₂ | 0.2<br>0.02 | 180'<br>180'=0% |
| (B) (known) O₂N–C₆H₄–C(=N-OC₂H₅)–O–P(S)(OC₂H₅)₂ | 0.2 | 180'=0% |
| (I) 2-NO₂-C₆H₄–C(=N-OCH₃)–O–P(S)(OC₂H₅)₂ | 0.002 | 120' |

EXAMPLE 8 a. The N-methyloxy-2-nitrobenzhydroxamic acid

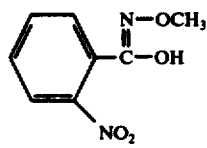

which was to be used as the starting material was prepared as follows:

186 g (2.2 moles) of O-methylhydroxylamine hydrochloride, dissolved in 322 ml of water, were added dropwise at 10° C to 322 g (2.32 moles) of potassium carbonate dissolved in 276 ml of water. 340 g (1.84 moles) of 2-nitrobenzoyl chloride were added dropwise to this mixture. After stirring the batch for one hour, the residue was filtered off and was suspended in lukewarm water in order to dissolve the admixed potassium chloride. The solid constituents were again filtered off and washed with water. 192 g (53% of theory) of N-methoxy-2-nitro-benzhydroxamic acid were obtained as a slightly granular beige-colored powder of melting point 104° C (which can be recrystallized from ethyl acetate).

b)

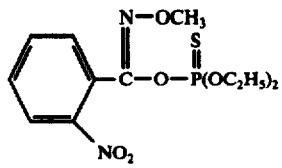

98 g (0.5 mole, melting point 104° C) of N-methoxy-2-nitrobenzhydroxamic acid were dissolved in 320 ml of acetonitrile. After adding 82 g (0.59 mole) of finely powered potassium carbonate, the mixture was warmed to 50° C, while stirring, and at this temperature 84.5 g (0.45 mole) of O,O-diethylthionophosphoric acid diester chloride were added dropwise. The mixture was warmed to 50° C for 20 hours, with continued stirring. After it had cooled, the batch was poured into water and the oil which separated out was taken up in toluene. The aqueous phase was separated off and the organic solution was washed first with water, then twice with 2 N sodium hydroxide solution and then again with water until it gave a neutral reaction, and was dried over sodium sulfate, and the solvent was distilled off. 120 g (76% of theory) of a yellowish oil, which tended to crystallize slowly, remained. The crystals were pressed out on clay and were briefly covered with ice-cold isopropanol. O,O-Diethyl-O-(N-methoxy-2-nitrobenzimidoyl)-thionophosphoric acid ester was thus obtained in coarse, yellow crystals of melting point 65° C.

EXAMPLE 9

980 g (5 moles) of N-methoxy-2-nitrobenzhydroxamic acid were dissolved in 3.2 liters of acetonitrile. After introducing 820 g (5.96 moles) of ground potassium chloride, the mixture was warmed for half an hour to 50° C and 845 g (0.448 mole) of O,O-diethylthionophosphoric acid diester chloride were then added, while cooling with water, at a speed such that a temperature of 50° C was maintained. The batch was stirred for 20 hours at 50° C, was allowed to cool and was then poured into a large amount of water. Thereupon, crystallization rapidly occurred. The crystals were suction-drained thoroughly and the residue was dissolved in 1.2 liters of warm isopropanol. On stirring the solution, while cooling with ice water, the O,O-diethyl-O-(N-methoxy-2-nitrobenzimidoyl)-thionophosphoric acid ester crystallized as a pale yellow crystal powder of melting point 65° C.

It will be appreciated that the instant specification and examples are set forth by way of illustration and not limitation, and that various modifications and changes may be made without departing from the spirit and scope of the present invention.

What is claimed is:

1. O,O-Diethyl-O-(N-methoxy-2-nitrobenzimidoyl)-thionophosphoric acid ester of the formula

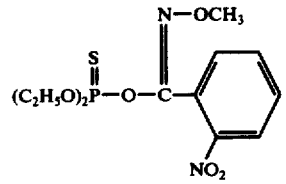

2. An insecticidal or acaricidal composition containing as active ingredient an insecticidally or acaricidally effective amount of a compound according to claim 1 in admixture with a diluent.

3. A method of combating insect or acarid pests which comprises applying to the pests or a habitat thereof an insecticidally or acaricidally effective amount of a compound according to claim 1.

* * * * *